United States Patent [19]

Patrick et al.

[11] Patent Number: 5,222,506
[45] Date of Patent: Jun. 29, 1993

[54] IMPLANTABLE MEDICAL LEAD WITH ELECTRICAL CROSS-OVER ADAPTOR

[75] Inventors: Timothy Patrick, St. Paul; Richard D. Sandstrom, Scandia; Keith A. Ufford, Chisago City, Minn.

[73] Assignee: Medtronic, Inc., Minneapolis, Minn.

[21] Appl. No.: 736,858

[22] Filed: Jul. 29, 1991

[51] Int. Cl.⁵ ............................................. A61N 1/05
[52] U.S. Cl. .................................................. 128/784
[58] Field of Search ................................. 128/784-788

[56] References Cited

U.S. PATENT DOCUMENTS

| | | | |
|---|---|---|---|
| 4,214,594 | 7/1980 | Little | 128/786 |
| 4,236,525 | 12/1980 | Sluetz et al. | 128/786 |
| 4,413,636 | 11/1983 | Jasso | 128/786 |
| 4,759,378 | 7/1988 | Swendson et al. | 128/786 |
| 4,967,755 | 11/1990 | Pohndorf | 128/786 |

Primary Examiner—William E. Kamm
Attorney, Agent, or Firm—Reed A. Duthler; Harold R. Patton

[57] ABSTRACT

A cross-over adaptor for reversing the electrical connection of outer and inner coaxial coiled wire conductors is provided in the body of a pacing lead having a physiologic sensor incorporated therein so that the lead may be employed advantageously for conventional pacing functions with or without physiologic sensor function. In a specific embodiment, the adaptor is placed adjacent to a physiologic pressure sensor positioned in line in the lead body between the connector end thereof and the distal pace/sense electrode end thereof. The physiologic pressure sensor possesses an elongated cylindrical outer housing and an axially oriented electrical feed-through to the active components thereof. The cross-over adaptor is coupled at one end thereof to the sensor housing and electrical feed-through and at the other end thereof to the inner and outer coaxial coiled wire lead conductors which extend back to the proximal end of the lead body and are electrically connected to proximal pin and ring connector elements. At the distal end of the lead, the distal tip electrode is electrically coupled to the outer housing of the physiologic sensor. The electrical cross-over adaptor electrically connects the inner coiled wire conductor to the cylindrical housing of the physiologic sensor and the outer coiled wire conductor to the electrical feed-through of the physiologic sensor so that the proximal pin connector element is electrically connected to the distal tip electrode and the proximal ring connector element is electrically connected to the electrical feed-through of the physiological sensor. Thus, the electrical interconnection allows the lead to be employed as a conventional unipolar pacing lead in those situations where the physiological sensor is not employed in the pacing system.

17 Claims, 4 Drawing Sheets

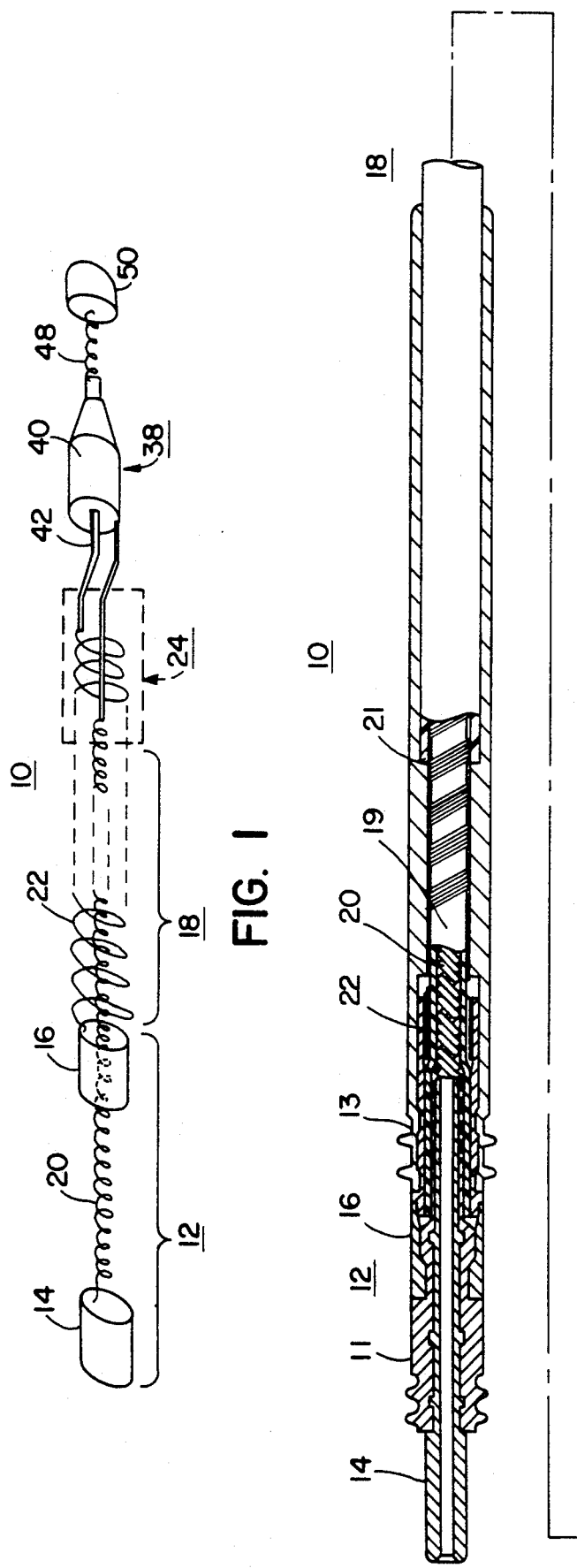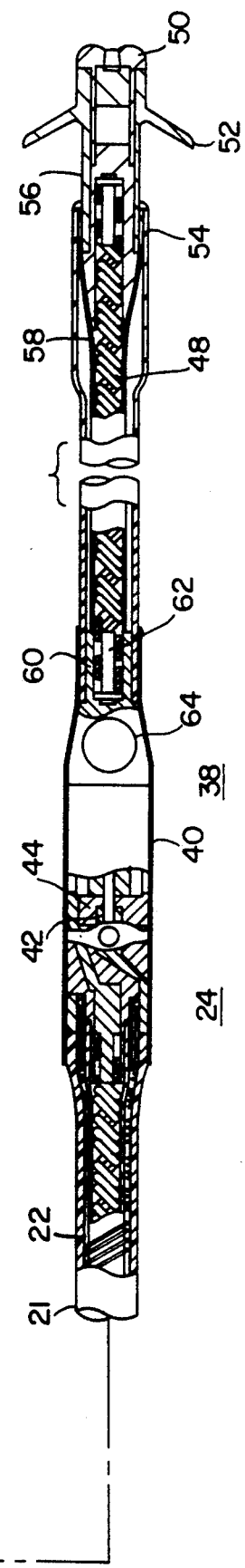
FIG. 1
FIG. 2

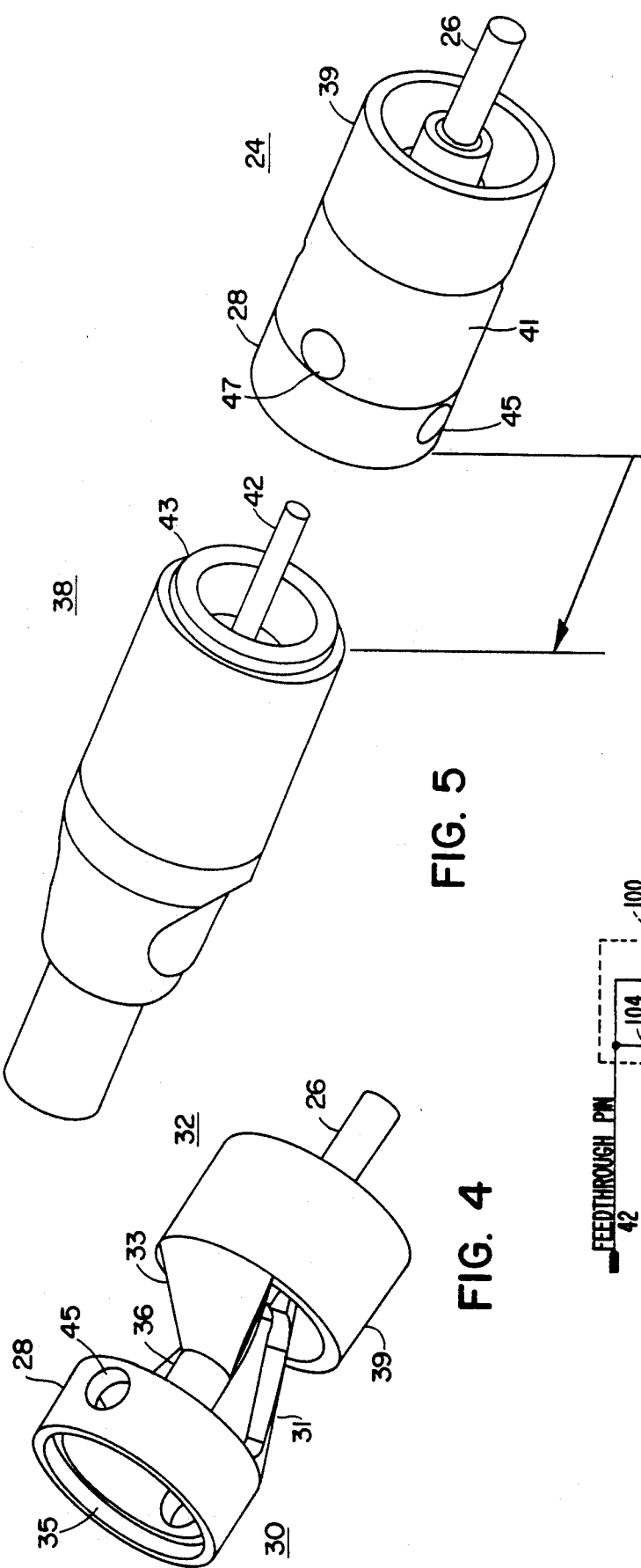
FIG. 5
FIG. 4
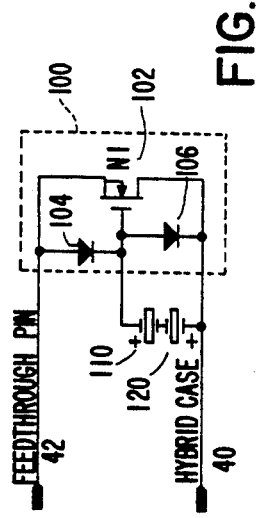
FIG. 9

IMPLANTABLE MEDICAL LEAD WITH ELECTRICAL CROSS-OVER ADAPTOR

BACKGROUND OF THE INVENTION

1. Field of the Invention

This invention relates to an improved mechanical interrelation of the components of an electrical medical lead system for allowing the reversal of the electrical interconnection of inner and outer coaxial coiled wire conductors with other components of the lead system, and particularly, for the use of such an adaptor in a pacing lead system having a physiologic sensor incorporated therein.

2. Brief Description of the Prior Art

Electrical medical lead systems of many types are known in the art and commonly comprise a proximal connector portion having one or more connector elements, an elongated insulated lead body having one or more mutually insulated electrical conductors extending therethrough and one or more mutually insulated electrodes arranged at or near the distal portion of the lead system. Electrical medical lead systems may be employed in pacing, neurologic stimulation, cardioversion/defibrillation and in numerous other applications where such lead systems are introduced temporarily or implanted permanently within the patient's body to provide an electrical interconnection between a site where electrical stimulation is to be delivered or electrical signals of the body are to be detected and a more remotely situated stimulator or sensing apparatus.

In such lead systems, coiled wire conductors have been employed for many years, originally in side by-side relation and more recently in coaxial relation to one another. Also more recently, it has become common to incorporate physiologic sensors, such as blood pressure sensors, oxygen sensors, temperature sensors, or the like, within the lead body for providing physiologic monitoring of the selected parameter in conjunction with the sensing of electrical events and the delivery of electrical stimulation. In the pacing context, for example, numerous sensors have been incorporated in lead bodies, including those enumerated in the article entitled "Principles of Exercise Responsive Pacemakers," *IEEE Engineering in Medicine and Biology*, June 1984, pp. 25-29, by Fearnot, N.E. et al. Further sensors are enumerated in the article entitled "Research Leads to Major Breakthrough in Rate Responsive Pacemaking," by Kenneth M. Anderson on pp. 89-93 of *Medical Electronics* of October 1986.

Such sensing systems for both pacing and cardioversion systems include pressure sensors incorporated into housings positioned along the lead body as disclosed in U.S. Pat. Nos. 4,407,296 to Anderson, and 4,485,813 to Anderson et al, incorporated herein by reference in their entireties. Considerable activity has also been expended in the incorporation of oxygen sensors in pacing and cardioversion leads, as shown, for example, in U.S. Pat. No. 4,815,469 to Cohen, et al, and patents referenced therein.

A number of design constraints are placed on the characteristics of the materials used in and the physical size of components of modern pacing and cardioversion leads. Incorporation of physiologic sensors into these lead systems adds complexity and increases reliability issues concerning the size, performance, and longevity of the lead system. The above-referenced '296, '813 and '469 patents attempt to address the manner in which the electrical interconnections are effected in a pacing lead in the presence of a relatively bulky pressure or oxygen sensor. It is desirable to accommodate pacing or cardioversion and sensing functions employing the minimum number of electrical conductors and associated connector elements while maintaining operational flexibility in the use of the elements of the system, high reliability, and over all lead flexibility and handling characteristics desired by the physician users.

With these considerations in mind, the '813 patent addresses the reduction of the number of lead conductors and associated connector elements to allow for connecting at least one pace/sense distal electrode and the distally located pressure sensor to a pacing pulse generator. The pressure sensor disclosed therein is cylindrical in shape and its outer conductive housing constitutes one of the electrical signal return paths of the sensor transducer located therein by a conductor connected thereto. The active circuit components of the pressure sensor are connected by a feed-through extending axially from one end of the housing to a separate conductor.

Although not specifically described in the '813 patent, leads constructed in accordance with its teachings and implanted in clinical testing were constructed with co-axial inner and outer coiled wire conductors. The inner and outer coiled wire conductors were connected distally to the feed-through and cylindrical housing, respectively, of the pressure sensor and proximally either to proximal pin and ring shaped, in-line connector elements, respectively, or to bifurcated connector pins. The distal tip pace/sense electrode was connected by a short conductor coil to the cylindrical housing of the pressure sensor, and both were insulated from the body environment. Thus the tip electrode was connected to the ring shaped, in line connector element or one of the bifurcated connector pins.

The '469 patent addresses a number of approaches to the interconnection of the pace/sense electrodes with the active components and housing of an oxygen sensor within a pacing lead body. The lead system depicted therein employs side-by-side coiled wire conductors for providing an electrical connection between the active components of the sensor and the pacing electrodes, where the coiled wire conductors pass through apertures within the sensor housing or are electrically connected to the sensor housing in order to interconnect the active sensor components and the pace/sense electrodes with appropriate connector elements at the proximal end of the lead. Although one embodiment depicts the employment of a pair of coaxially oriented coiled wire conductors, they extend through the sensor housing to interconnect distal tip and ring pace/sense electrodes with proximal connector elements. A separate, parallel oriented, coiled wire conductor is interconnected with the feed-through of the active components of the sensor and a proximal connector element.

It is generally undesirable to employ coiled wire conductors extending the length of the lead body in parallel or side-by-side relation in view of problems that may arise in the unequal flexing forces applied to the side-by-side coiled wire conductors when the lead is implanted. In a multi-filar, coiled wire conductor lead system employing modern conductor diameters, it is preferred to employ a coaxial arrangement as described above. However, the use of the coaxial conductors extending from the proximal connector elements of an in-line connector to the distal components of the lead normally requires that the inner conductor be electrically connected to the proximal most connector element or pin and the outer conductor or conductors be connected to the more distally located connector elements. Since the lead body is desirably cylindrical throughout its length and the sensor housings are likewise cylindrical, the outer conductor is normally connected to the sensor housing and the inner conductor is connected to the active elements of the sensor through its feed-through, which extends axially with respect to the lead body all as described above.

In order to allow replacement of pacing pulse generators with pacing leads already implanted in a patient, each manufacturer initially developed its own size and spacing convention for its pulse generator connector elements and leads, connector pins, rings and insulators. Subsequently, an industry-wide standard was proposed for specifying the size and location of connector elements on lead bodies and within the connector blocks of in-line connector pacing pulse generators to allow interchangeability of pacing lead and pulse generator products within the industry. A precursor to this standard was set forth in the article entitled "A Voluntary Standard For 3.2 mm Unipolar and Bipolar Pacemaker Leads and Connectors," by Calfee, et al, *PACE*, Vol. 9, pp. 1181-1185, 1986, incorporated herein by reference in its entirety. The current draft standard (ISL DIS 5841 3.3) is popularly referred to as the "IS-1" Connector Standard. Lead connectors conforming to the IS-1 Connector Standard are disclosed in U.S. Pat. Nos. 4,951,687 and 5,007,435, incorporated herein by reference in their entireties.

The IS-1 standard dictates that the proximal-most connector pin of the in-line connector be coupled electrically with the distal-most pace/sense electrode of a pacing lead system. Since the proximal pin connector element is coupled to the inner coaxial coiled conductor, the bulk of the sensor body obstructs the connection of the inner coil conductor to the distal tip electrode.

SUMMARY OF THE INVENTION

It is therefore an object of the present invention to provide a simple and efficient electrical cross-over adaptor for reversing the electrical orientation of inner and outer conductors of a coaxial coiled wire conductor lead system.

It is a further object of the present invention to provide an electrical cross-over adaptor for coupling an inner coiled wire conductor of a coaxial coiled wire conductor pair in a lead system to the outer housing of a sensor built into an electrical lead system and to connect the outer coil conductor to an axially aligned feed-through element of the sensor to enable the electrical connection of the proximal end of the inner coil conductor with components distal to the sensor in the lead.

These and other objects of the present invention are accomplished with an electrical cross-over adaptor having first and second cross-over components or members which are arranged to nest together without touching each other. The two nested components are advantageously molded together with an insulating compound to form a single part which then can be welded, crimped and/or staked to appropriate coils, wires or other parts to make the electrical cross-over connection.

In accordance with the preferred embodiment of the present invention, the first and second cross-over components each possess a first ring-shaped member having an inside diameter generally corresponding to the outside diameter of the outer coaxial coiled conductor or an outside diameter corresponding to the outer diameter of the cylindrical housing of the sensor, a reduced diameter pin or socket positioned axially with respect to the axis of the sensor feed-through or the inner coil conductor and respective conically tapered sections which electrically and mechanically connect the respective ring and pin elements.

The electrical cross-over adaptor of the present invention advantageously retains the ability to employ coaxial, multi-filar, coiled wire conductor pairs, avoids invading the space of the physiological sensor and satisfies conventions for electrodes and connector elements. The electrical cross-over adaptor of the present invention is also advantageously compact and avoids the necessity for an adaptor in the event that the sensor fails or is not used for one reason or another.

BRIEF DESCRIPTION OF THE DRAWINGS

The above and other objects and advantages of the present invention will be more clearly understood by reference to the following description and the accompanying drawings, in which like referenced numerals designate like parts throughout the figures thereof and wherein:

FIG. 1 is a simplified schematic illustration of a body implantable lead system in which the electrical cross-over adaptor of the present invention is implemented;

FIG. 2 is a cross-sectional view of a pacing lead in which the electrical cross-adaptor of the present invention is implemented in conjunction with a physiologic pressure sensor;

FIG. 4 is a perspective view of the assembly of the first and second conical-shaped nesting members of the electrical cross over adaptor;

FIG. 5 is a perspective view of the orientation and interconnection of the electrical cross-over adaptor to the housing and feed-through of the physiologic sensor in accordance with the present invention;

FIG. 9 is a schematic diagram of the pressure sensor hybrid circuit preferably incorporated into the pressure sensor of the FIG. 2 lead embodiment.

DESCRIPTION OF THE PREFERRED EMBODIMENTS

Figure 3:
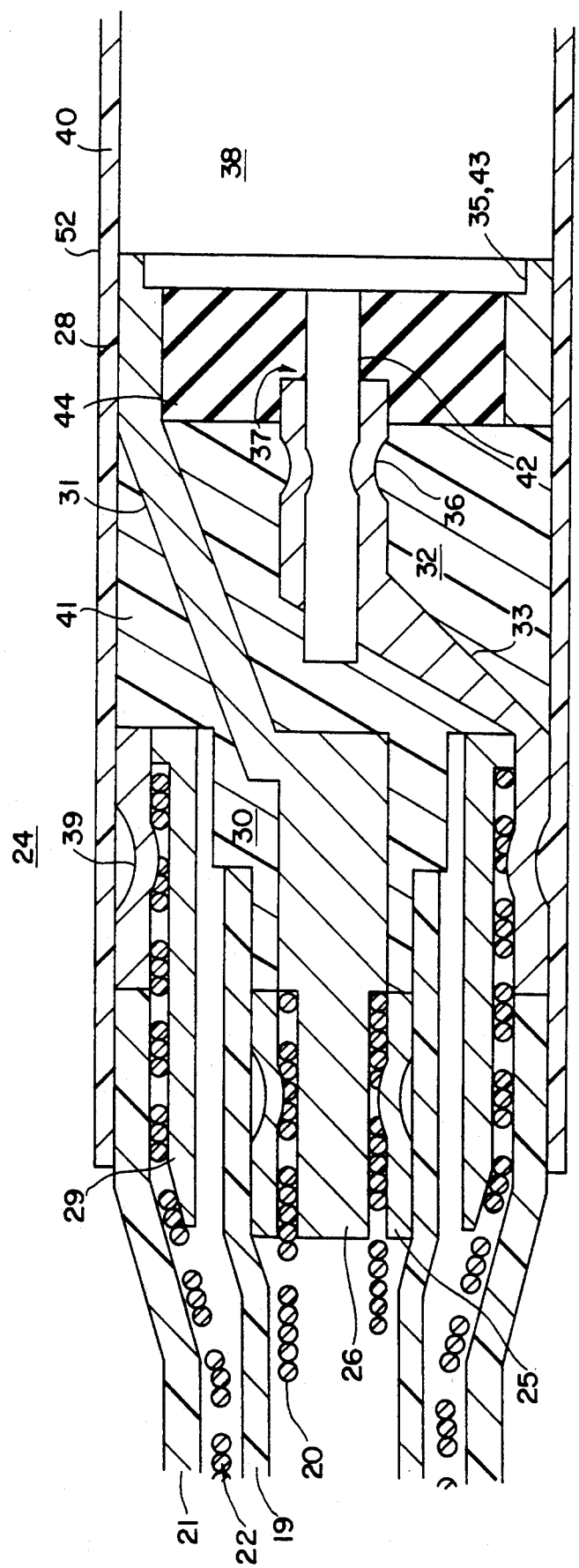
FIG. 3 is an enlargement of a portion of the cross-section of the lead depicted in FIG. 2 showing the electrical connection of the distal portions of the inner and outer coaxial coiled wire conductors to one end of the electrical cross-over adaptor assembly and the connection of the physiological sensor feed-through and housing to the other end of the adaptor.

Turning now to FIGS. 1 and 2, they depict in schematic and side elevation views a preferred embodiment of the lead system in which the electrical cross-over adaptor of the present invention may be implemented. It will be understood that the electrical cross-over adaptor of the present invention may find other uses than in conjunction with the specific pacing lead and pressure sensor embodiment described in conjunction with FIGS. 1 and 2. FIG. 1 is a simplified schematic illustration of the interconnection of the tip electrode of a pacing lead with the proximal-most pin connector element thereof through the use of electrical cross-over adaptor for reversing the electrical interconnection of inner and outer coiled wire conductors at the interface of the adaptor with a physiologic sensor located in the distal portion of the lead. FIG. 2 depicts this relationship in a cross-sectional view of an actual lead embodying the physical components of the schematically illustrated interconnection of FIG. 1.

In FIG. 1, the lead 10 comprises a proximal connector portion 12 having a proximal tip connector pin 14 and a more distally located ring connector element 16, an elongated lead body 18 which comprises an inner coiled wire conductor 20 connected proximally to the pin connector element 14 and a coaxially arranged outer coiled wire conductor 22 electrically connected proximally at the ring connector element 16. The elongated lead body 18 including the inner and outer coaxial coil wire conductors 20 and 22, extends to the proximal side of the electrical cross-over adaptor 24. The electrical cross-over adaptor 24 is connected in turn to the physiologic sensor 38. Specifically, the distal ends of the outer conductor coil 22 and the inner conductor coil 20 are respectively electrically connected by electrical cross-over adaptor 24 to the active circuit elements and the outer case of the sensor 38. An axially disposed feed-through pin 42 provides access to the active components of the sensor 38.

The lead 10 includes a distal tip electrode 50 adapted to be used as a pacing and sensing electrode in a patient's heart, which is electrically connected through coiled wire conductor 48 to the electrically conductive outer case 40 of the sensor 38. Thus, an electrical connection extends from the proximal pin connector element 14 through conductor 20, cross-over adaptor 24, conductive housing 40 and conductor 48 to tip electrode 50 for normal unipolar pacing and sensing operations. The electrical interconnection of the active components of the physiologic sensor 38 to a pacemaker adapted to employ the physiologic signal detected thereby is effected by the ring connector element 16, outer coaxial conductor coil 22, electrical cross-over adaptor 24 and feed-through 42.

Referring now to FIG. 2, it depicts in partial cross-section an actual lead embodying the concepts of the present invention and illustrates in conjunction with the remaining figures the best mode of practicing the invention known to the inventors at the time of filing of the application. In FIG. 2, the proximal connector portion 12, a portion of the lead body 18, the electrical cross-over adaptor 24, the pressure sensor 38 and the distal conductor 48 and electrode 50 are depicted. The proximal connector 12 includes the proximal pin connector element 14 and ring connector element 16 with associated, ribbed insulating sleeves 11 and 13 configured to conform to the proposed IS-1 standard. The proximal pin connector element 14 extends axially within the lead body to a position inside the insulating ribs 13 where it is electrically and mechanically connected to the inner coiled wire conductor 20 in a fashion known in the prior art. The inner coiled wire conductor 20 may be wound of a number, such as five, of filar elements as more clearly shown in FIG. 3 and forms a lumen within which a stylet may be extended to stiffen the lead body during implantation in a fashion well known in the prior art. The inner coiled wire conductor 20 may be insulated by a tube of insulating material 19 as is known in the art.

The outer conductor coil 22 is similarly preferably constructed of multi-filar wire turns as shown more clearly in FIG. 3, and is electrically and mechanically connected to ring connector element 16 in a fashion well known in the prior art. An outer insulating tube or pair of coaxial tubes 21 overlies the outer coaxial coiled wire conductor 22 throughout the length of the lead body 18 in a fashion well known in the prior art.

The distal portion of the lead depicted in FIG. 2 includes the distal tip electrode 50 which preferably is constructed to provide for the slow release of anti-inflammatory steroids from a steroid retaining body located inside the distal tip assembly according to the disclosure in U.S. Pat. No. 4,506,680, issued to Stokes, and incorporated herein by reference in its entirety. Electrode 50 is held in place within the heart by means of pliant tines 52, which are more fully described in U.S. Pat. No. 3,902,501, issued to Citron et al, also incorporated herein by reference in its entirety. The tip electrode 50 is electrically connected to the distal coiled wire conductor 48 which extends proximally to a necked-down section of the exterior surface 40 of the pressure sensor 38. The conductor 48 is insulated by an insulating sheath 54 which overlies a proximal portion of the tine assembly 52 which insulates the inner components, including the connector pin 56, and the inner insulating layer 58. The coiled wire conductor 48 is electrically connected to the necked-down portion 60 of the outer surface 40 of the sensor 38 by crimping necked-down portion 60, coiled wire conductor 48 and pin 62 in a fashion well known in the prior art.

The specific component configurations, fabrication techniques and materials used in the construction of the lead of FIG. 2, as described so far, may follow the teachings of the above incorporated '687, '435 and '680 patents or U.S. Pat. Nos. 4,428,725 to O'Neill and 4,328,812 to Ufford et al, also incorporated herein by reference in their entireties.

Turning now to the pressure sensor 38, it may advantageously employ the circuits 50, 52 of and operate in the same fashion as the pressure sensor depicted and described in the above incorporated '813 patent although it preferably employs the hybrid circuit of FIG. 9 rather than the circuit 50. FIG. 9 depicts a further pressure sensor electronic circuit preferably employed in the lead of FIG. 2 that differs somewhat from the circuit 50 of the '813 patent. The FIG. 9 circuit possesses a pair of series-connected, oppositely poled, two terminal piezoelectric crystals 110, 120 in the capsule within the pressure sensor 38. Crystal 120 is mounted on one face on the sensor diaphragm membrane and crystal 110 is mounted on its other face to provide temperature compensation by offsetting temperature induced voltages affecting both crystals 110, 120. The crystal 120, biased by diodes 104, 106 during periodic energization of the circuit through pin 42, produce a voltage on the gate of FET 102 proportional to the mechanical deflection of a membrane supporting the crystals. The instantaneous voltage at the gate of FET 102 is reflected as a drain to-source voltage proportional thereto. The variations in drain-to-source voltage are processed in the fashion described in the above incorporated '813 patent. FIG. 9 depicts one of many sensor elements, including temperature, blood flow, blood gas or the like, and associated circuits that may advantageously be employed in the practice of the present invention.

Returning to FIG. 2, a port 64 in the necked-down portion of the outer housing 40 of the sensor 38 provides fluid communication to the flexible diaphragm membrane of the pressure and motion-sensing capsule located within housing 40 as described more specifically in the '813 patent. The electrical connections to the components within the capsule of the sensor 38 are effected by the electrically conductive outer housing surface 40 and the insulated feed-through element 42 extending proximally from the proximal end of the sensor 38.

The above incorporated '813 patent shows the electrical interconnection of first and second lead conductor wires to the axially oriented feed through element and the outer housing but does not explain how the connector elements are connected with either of the conductors. In practice, the lead depicted in the '813 patent employed coaxially oriented multi-filar lead conductors and the tip electrode was electrically connected with the conductive housing of the pressure sensor. The tip electrode was thus electrically connected through the housing of the pressure sensor to the outer coaxial conductor wire and to the more distally located connector ring element or through a bifurcated proximal connector assembly to a separate connector pin. No attempt was made to provide an electrical connection to the proximal connector pin element of an in-line connector assembly satisfying the IS-1 connector standard.

In accordance with the present invention, the electrical cross over adaptor is implemented in the embodiment depicted in FIGS. 1 and 2 in order to provide for the electrical transposition of the relationship of the inner and outer conductor coils to allow for the satisfaction of the IS-1 connector standard in a simple, economical and reliable fashion.

Turning now to FIG. 3, the electrical cross over adaptor is depicted in a simplified, expanded cross sectional view of the portion of the drawing of FIG. 2 for ease of explanation in conjunction with the remaining FIGS. 4 through 8.

In FIG. 3, the inner and outer coaxial coiled wire conductors 20 and 22 are shown in engagement with first and second cross-over nesting members 30 and 32, respectively, which, when assembled together through the use of insulating polymer material 41, constitute the electrical cross-over adaptor. In reference to FIG. 4, it may be seen that the first and second conical-shaped nesting members 30 and 32 comprise respective axial pin elements 26 and 36, ring elements 28 and 39 and conical-shaped extension members 31 and 33, respectively interconnecting the ring and pin elements 30, 26 and 36, 39.

Referring back to FIG. 3, the first and second members 30 and 32 are shown in fully assembled relation with the distal ends of the inner and outer coiled wire conductors 20 and 22, respectively, and with respect to the feed-through terminal pin 42 and outer housing surface 40 of the sensor 38. The inner and outer coiled wire conductors 20 and 22 are electrically and mechanically connected to the pin 26 and ring 39 elements by employing a crimping ring 25 and crimping turns of the multi filar conductor coil 20 against the outer surface of the pin element 26 in a well known fashion. Similarly, the distal end of the outer coiled wire conductor 22 is coupled electrically and mechanically to the ring element 39 by providing a further crimping support ring 29 within the expanded turns of the outer coiled wire conductor and crimping the turns therebetween as shown in FIG. 3.

The interconnection of the pressure sensor 38 with the electrical cross over adaptor 24 is effected by slipping the feed through connector pin 42 into the recess 37 within the pin 36 of the second conical shaped nesting member 32 and a beveled end portion 43 of the outer housing 40 into the recess 35 of the ring element 28. Thereafter, the pin 36 is crimped onto the feed through pin 42 and the mating surfaces of the recesses 35 and 43 are laser welded together.

In reference to FIGS. 3, 4 and 5, the mating surfaces 35 and 43 are illustrated along with molded access holes 47 which allow for the introduction of crimping tools to effect the crimping together of the pin 36 and feed-through pin 42 and also access holes 45 in ring element 28, which allow for the introduction of insulating compound 44 after ring element 28 is welded to outer housing 40.

Figure 7A:
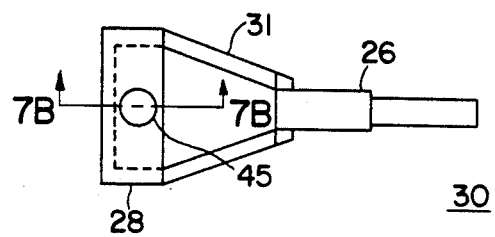
FIGS. 7A, 7B and 7C are elevation, cross section and end views of the second cross-over nesting member of the electrical cross-over adaptor.
Figure 7B:
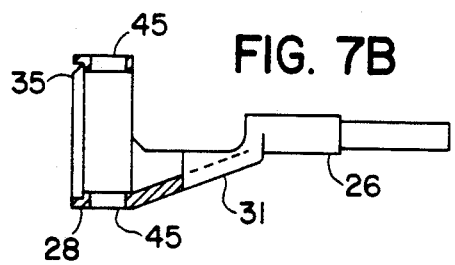
Figure 7C:
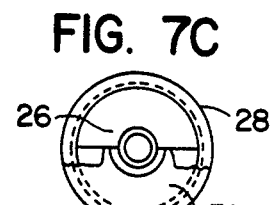
Figure 8A:
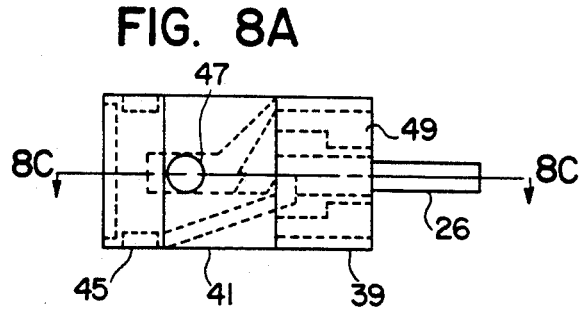
FIGS. 8A, 8B and 8C are elevation, cross-section and end views of the first and second cross-over nesting members assembled together with an insulating material to form the electrical cross over adaptor of the present invention incorporated within the lead assembly depicted in FIGS. 2 and 3.
Figure 8C:
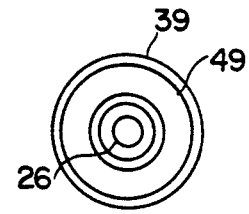

Referring now to FIGS. 6A-8C, they illustrate the second cross-over nesting element 32, the first cross over nesting element 30, and the assembled electrical cross-over adaptor 24 in various views. It will be understood that the first and second cross-over nesting elements 30 and 32 are assembled together as depicted in FIGS. 8A-8C through the use of an insulating compound 41 prior to its assembly into the lead as described above in reference to FIGS. 3 to 5.

Figure 6A:
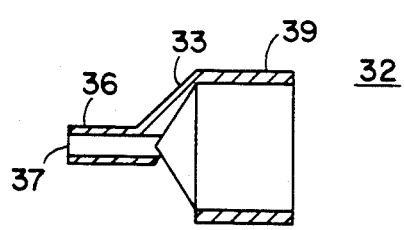
FIGS. 6A and 6B are cross-sectional and end views of the first cross-over nesting member of the electrical cross-over adaptor.
Figure 6B:
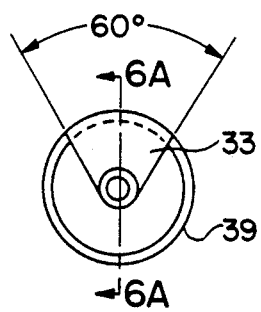

FIG. 6A is a cross-sectional view along the lines A—A of the cross over member 32 FIG. 6B. In FIG. 6A, it may be seen that the cross over member 32 is a generally funnel or conically shaped element having a cut out section of the conical portion of the funnel leaving about a 60° section that forms the conical portion 33.

Turning now to FIG. 7A, it depicts a side elevation view of the first cross-over nesting member 30. The member 30, as described above, includes the axially extending pin element 26, the funnel- or conically-shaped element 31 and the ring-shaped element 28 as well as the access holes 45 extending therethrough.

FIG. 7B depicts a partial cross-sectional view of the first member 30 along lines B—B of FIG. 7A, and FIG. 7C is an end view of the first member 30. The conical-shaped transition member 31 extends about 180° around the ring shaped element 28 as depicted in FIG. 7C.

Figure 8B:
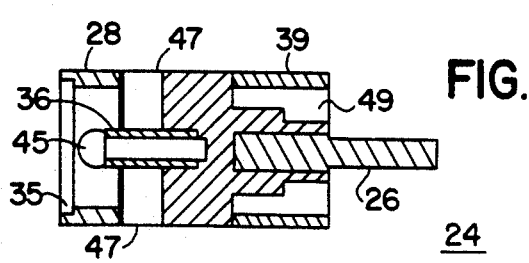

FIGS. 8A and 8C are side elevation and end views of the assembled electrical cross-over adaptor 24, and FIG. 8B is a cross-section view taken along the lines C—C of FIG. 8A.

FIG. 8A illustrates the presence of access holes 47 formed in molding the insulating material 41 to provide crimping tool access to the opposite surfaces of the pin element 36 to provide the crimps therein during assembly as illustrated in FIG. 3. FIGS. 8A and 8B also illustrate the presence of cylindrical recesses 49 in the material 41 which allow for the introduction of the crimping ring 29 inside the distal end of the outer coil conductor 22 during assembly, as depicted in FIG. 3. The outer surface of ring 39 is directly accessible for crimping without the necessity of providing any access thereto.

Thus, when the two cross-over members 30 and 32 are nested together in the configuration depicted in FIGS. 3 and 8A-8C, the conical-shaped transition members 31 and 33 are spaced apart from one another. The cross-over members 30 and 32 are maintained in that spaced-apart orientation by filling the space therebetween with nonconductive elastomeric polymer material filling space designated 41, the outline of which is described above and illustrated in FIGS. 8A to 8C.

The elastomeric polymer material 41 may be molded using bio-compatible poly-ether urethanes, e.g. Pellathane ® 2363-75D, or other bio-compatible insulating materials. The cross-over members 30 and 32 are preferably machined from titanium and platinum-iridium alloy, respectively, or other body-compatible conductive materials employed in implantable medical lead systems. The preferred material of member 30 corresponds to the material of the housing 40 to facilitate laser welding of the respective nesting surfaces 35 and 43 of the member 30 and sensor housing 40.

The electrical cross-over adaptor described above and depicted in the appended drawings may have other applications apparent to those having skill in the art than in the lead system of the preferred embodiment depicted above. Modifications of the preferred embodiments of the pacing lead and the cross-over adaptor described above will become readily apparent to those skilled in the art in light of the foregoing disclosure. For example, although only two cross-over nesting members are depicted and described, three or more such members may be envisaged to accommodate three or more co axial coiled wire conductors. Therefore, the scope of the present invention should be interpreted solely from the following claims as such claims are written in light of the disclosure.

What is claimed is:

1. In an electrical medical lead having a proximal portion, a distal portion and an intermediate portion, an electrical connector comprising a pair of connector elements disposed on said proximal portion, an electrode disposed on said distal portion, a physiologic sensor disposed between said electrode and said connector elements, said physiologic sensor having a generally axially disposed electrical feedthrough and a generally peripherally disposed housing, a pair of coaxial, inner and outer coiled wire conductors extending distally from said pair of connector elements through said intermediate portion and to said sensor and conductive means for coupling said electrode to said housing of said sensor, the improvement comprising electrical cross-over adaptor means for coupling said feedthrough with said outer coiled wire conductor and for coupling said conductive housing with said inner coiled wire conductor.

2. The medical lead of claim 1 wherein said cross-over adapter means further comprises:
a peripherally disposed conductive element and a centrally disposed conductive element insulated from said peripherally disposed conductive element and means for coupling said feedthrough with said axially disposed conductive element and for coupling said housing with said peripherally disposed conductive element, said axially disposed conductive element coupled to said outer coiled wire and said peripherally disposed conductive element coupled to said inner coiled wire conductor.

3. The medical lead of claim 1 wherein said electrical cross-over adapter means comprises:
a first conductive cross-over member having a first portion electrically connected to said generally peripherally disposed housing of said physiologic sensor, a generally axially disposed pin shaped portion electrically and mechanically coupled to said inner coiled wire conductor and a generally conical-shaped transition portion extending therebetween;
a second conductive cross-over member having a first portion electrically and mechanically coupled to said outer coiled wire conductor, a generally axially disposed pin-shaped portion electrically and mechanically coupled to said feedthrough of said physiologic sensor and a generally conically shaped transition portion extending therebetween; and
means for nesting said first and second cross-over members together while electrically isolating the components of each from the other.

4. The medical lead of claim 3 wherein said electrical connector elements comprise first and second electrical connectors, said first electrical connector located proximal to said second electrical connector, further comprising:
means for electrically connecting said inner coiled wire conductor to said first electrical connector.

5. The medical electrical lead of claim 4 wherein said generally conically shaped transition portions of said first and second cross-over members are provided with cut out sections to enable the nesting together of said first and second cross-over members while spacing said generally conically shaped transition portions of said first and second cross-over members apart from one another.

6. The electrical medical lead of claim 5 further comprising molded polymeric material means for spacing and electrically insulating all portions of said cross-over members from one another.

7. The medical lead of claim 6 wherein said first portions of said first and second cross-over members comprise ring-shaped elements.

8. The medical lead of claim 1 wherein said electrical cross-over adapter comprises:
a first cross-over member having a generally peripherally disposed portion, a generally axially disposed portion electrically and mechanically connected to said inner coiled wire conductor and a generally conical shaped transition portion extending therebetween;
a second cross-over member having a generally peripherally disposed portion electrically and mechanically coupled to said outer coiled wire conductor, a generally axially disposed portion and a generally conical shaped transition portion extending therebetween; and
means for nesting said first and second cross-over members together while electrically insulating components of each from the other to form an integral electrical cross-over adapter.

9. The medical lead of claim 8 wherein:
said pair of connector elements comprise a first connector element located proximal to a second connector element, and wherein said lead further comprises means for electrically connecting said inner coiled wire conductor to said first connector element.

10. The medical lead of claim 9 wherein said generally conically shaped transition portions are provided with cut-out sections to enable the nesting together of said first and second cross members while spacing the generally conically shaped transition portions of said first and second cross-over members apart from one another.

11. The electrical medical lead of claim 10 further comprising molded polymer means for spacing and electrically insulating said cross-over members from one another.

12. The medical lead of claim 8 wherein said generally peripherally disposed portions of said first and second cross-over members comprise ring-shaped elements.

13. A medical electrical lead, comprising:
an elongated lead body having a proximal end and a distal end;
first and second electrical connectors mounted adjacent the distal end of said lead body;
inner and outer coiled wire conductors extending proximately within said lead body from said first and second electrical connectors respectively;
a physiologic sensor mounted to said lead body distal to said first and second connector elements, said physiologic sensor having a generally axially disposed electrical feedthrough and a generally peripherally disposed housing; and
electrical cross-over adapter means for coupling said outer coiled wire conductor to said feedthrough and for coupling said inner coiled conductor to said housing.

14. A lead according to claim 13 wherein said first connector element is located proximal to said second connector element.

15. A lead according to claim 13 or claim 14 further comprising an electrode mounted to said lead body distal to said sensor and conductive means for electrically coupling said electrode to said housing.

16. A lead according to claim 13 or claim 14 wherein said cross-over adapter means comprises a first cross-over member having a first, ring-shaped portion connected to said housing and a second portion extending proximally to said ring shaped portion, said cross-over adapter means further comprising a second cross-over member having a ring shaped portion electrically coupled to said outer coiled wire conductor, located concentrically around said proximally extending portion of said first cross-over member, said second cross-over provided with a distally extending portion extending within said ring-shaped portion of said first cross-over member, and coupled to said feedthrough.

17. A lead according to claim 16 further comprising means for insulating said first cross-over member from said second cross-over member.

* * * * *